(12) United States Patent
Safai

(10) Patent No.: US 6,605,807 B2
(45) Date of Patent: Aug. 12, 2003

(54) INFRARED CRACK DETECTION APPARATUS AND METHOD

(75) Inventor: Morteza Safai, Seattle, WA (US)

(73) Assignee: The Boeing Company, Chicago, IL (US)

(*) Notice: Subject to any disclaimer, the term of this patent is extended or adjusted under 35 U.S.C. 154(b) by 12 days.

(21) Appl. No.: 10/267,491

(22) Filed: Oct. 9, 2002

(65) Prior Publication Data

US 2003/0030002 A1 Feb. 13, 2003

Related U.S. Application Data

(63) Continuation of application No. 09/587,423, filed on Jun. 5, 2000.

(51) Int. Cl.[7] .............................................. G01N 21/84
(52) U.S. Cl. ............................ 250/341.1; 250/341.8; 250/338.1; 250/359.1
(58) Field of Search .......................... 250/336.1, 338.1, 250/339.06, 341.6, 341.8, 358.1, 359.1, 341.1

(56) References Cited

U.S. PATENT DOCUMENTS

| 4,065,212 A | 12/1977 | Belleson et al. |
| 5,118,945 A | 6/1992 | Winschuh et al. |
| 5,278,635 A | 1/1994 | Ono et al. |
| 5,376,793 A | * 12/1994 | Lesniak ............... 250/341.8 |
| 5,654,977 A | 8/1997 | Morris |
| 5,699,153 A | 12/1997 | Takamoto et al. |
| 5,808,305 A | 9/1998 | Leidecker et al. |
| 5,894,345 A | 4/1999 | Takamoto et al. |

* cited by examiner

Primary Examiner—Constantine Hannaher
Assistant Examiner—Timothy J Moran
(74) Attorney, Agent, or Firm—Harness Dickey & Pierce P.L.C.

(57) ABSTRACT

A detection system for identifying surface irregularities such as cracks, pits, scratches and holes in a part that is made of a material having a relatively high reflectivity and a relatively low emissivity such as titanium, aluminum, and silicon (such as silicon solar panels). A laser source generates a laser beam having a diameter that is approximately 50 microns or less. A scanning device scans the laser beam across the surface of the part. A surface irregularity radiates energy from said laser beam. An infrared receiver is directed at the surface of the part. The infrared receiver generates an infrared signal of the surface. A display that is connected to the infrared receiver displays the infrared signal to identify surface irregularities. Preferably, the infrared receiver is oriented at a first angle relative to a line perpendicular to the surface of the part. The first angle is preferably greater than 20 degrees and less than 30 degrees. An image processing module performs image processing on the infrared signal. A peak detection image processor compares the infrared signal generated by the infrared receiver to a threshold signal and declares a surface irregularity when the infrared signal exceeds the threshold signal.

16 Claims, 2 Drawing Sheets

INFRARED CRACK DETECTION APPARATUS AND METHOD

CROSS-REFERENCE TO RELATED APPLICATIONS

This application is a continuation of U.S. patent application Ser. No. 09/587,423 filed on Jun. 5, 2000. The disclosure of the above application is incorporated herein by reference.

TECHNICAL FIELD OF THE INVENTION

This invention relates to the detection of cracks in manufactured parts. More particularly, this invention relates to the detection of surface cracks in parts made of materials having a highly reflective surface and a low emissivity.

BACKGROUND OF THE INVENTION

Manufacturers are often forced to optimize the design of parts that they manufacture in an effort to increase the efficiency of devices employing the parts. To that end, the design of the parts are optimized through the use of lighter weight materials and through the elimination of material that does not strengthen the part. The design optimization process assumes that the part is manufactured to exacting specifications.

Oftentimes, the optimized part includes complex geometric and curved surfaces which need to be manufactured. Manufacturers must identify parts that fail to meet the specifications in an efficient manner to control manufacturing costs. To reduce weight, manufacturers employ lighter weight materials such as aluminum, titanium and silicon which have a high reflectivity and a low emissivity. In order for these parts to perform as intended, the parts must be manufactured without surface irregularities such as cracks, pits, scratches and holes. If the surface irregularities are not found, the part may fail early which can be problematic if the part is critical to the safe operation of the device.

For example, aircraft manufactures currently manufacture complex geometric and curved aluminum stringers which can be 110 feet in length and 12 inches wide. These stringers are considered to be a critical structure of aircraft wings. After being manufactured, the stringer is transferred to a liquid penetrant inspection station for quality control. A liquid penetrant is applied to a surface of the part that is to be inspected. An operator inspects the part for surface irregularities. This technique is time consuming which increases the cost of the stringer and the time required to manufacture the stringer. The liquid penetrant that is applied to the stringer also contaminates the part.

Infrared crack detection involves applying a highly emissive material to a surface of the part to be inspected. The part is heated uniformly using a flash lamp or other suitable devices. The part absorbs or couples some of the energy contained in the flash. The coupled energy causes the entire part to radiate heat. If the part was manufactured perfectly, a thermal gradient for the part would vary in a continuous manner. Using an infrared camera, the thermal gradient of the part is measured. Abrupt discontinuities in the thermal gradient identify the surface irregularities such as surface cracks, pits, scratches and holes. This method fails to identify smaller cracks, scratches, and holes because the heat energy flows over the opening.

Unfortunately, the conventional infrared crack detection method cannot be used on aluminum having a thickness greater than approximately ⅛". Aluminum has relatively high heat dissipation characteristic. Therefore, if the aluminum part has a thickness, greater than ⅛", the heat generated by the flash lamp is quickly absorbed and dissipated by the aluminum. The thermal gradient does not adequately and reliably identify smaller surface irregularities such as cracks, pits, scratches and holes. If a higher energy source such as a laser is used, the emissive material is vaporized. If the highly emissive material is not used, an extremely high power laser is required to heat or couple with aluminum.

SUMMARY OF THE INVENTION

A detection system for identifying surface irregularities includes a part that is made of a material having a relatively high reflectivity in a relatively low emissivity. A laser source generates a laser beam. A scanning device scans the laser beam across a surface of the part. A surface irregularity radiates energy absorbed from said laser beam. An infrared receiver is directed at the surface of the part. The infrared receiver generates an infrared signal of the surface. A display that is connected to the infrared receiver displays the infrared signal to identify the surface irregularity.

In one feature of the invention, the scanning device directs the laser beam onto the part in an incident angle that is substantially perpendicular to the surface of the part.

In other features of the invention, the laser beam has a beam diameter that is approximately 50 microns or less. The infrared camera is oriented at a first angle relative to a line perpendicular to the surface of the part. The first angle is greater than 20 degrees and less than 30 degrees.

In still other features of the invention, a part transport device moves the part in a first direction. The scanning device scans the surface of the part in a second direction that is perpendicular to the first direction. An image processing module that is associated with the computer performs image processing on the infrared signal. A peak detection image processor associated with the computer identifies a surface irregularity by comparing the infrared signal generated by the infrared receiver through a threshold signal. The peak detection processor declares a surface irregularity when the infrared signal exceeds the threshold signal.

In yet another feature of the invention, the scanning device includes a first mirror and a second mirror. At least one of the first and second mirrors is rotatable and includes a plurality of facets for scanning the laser beam across the surface of the part.

Other objects, features and advantages will be readily apparent from the specification, the claims, and the drawings.

DETAILED DESCRIPTION OF THE PREFERRED EMBODIMENTS

Figure 1:
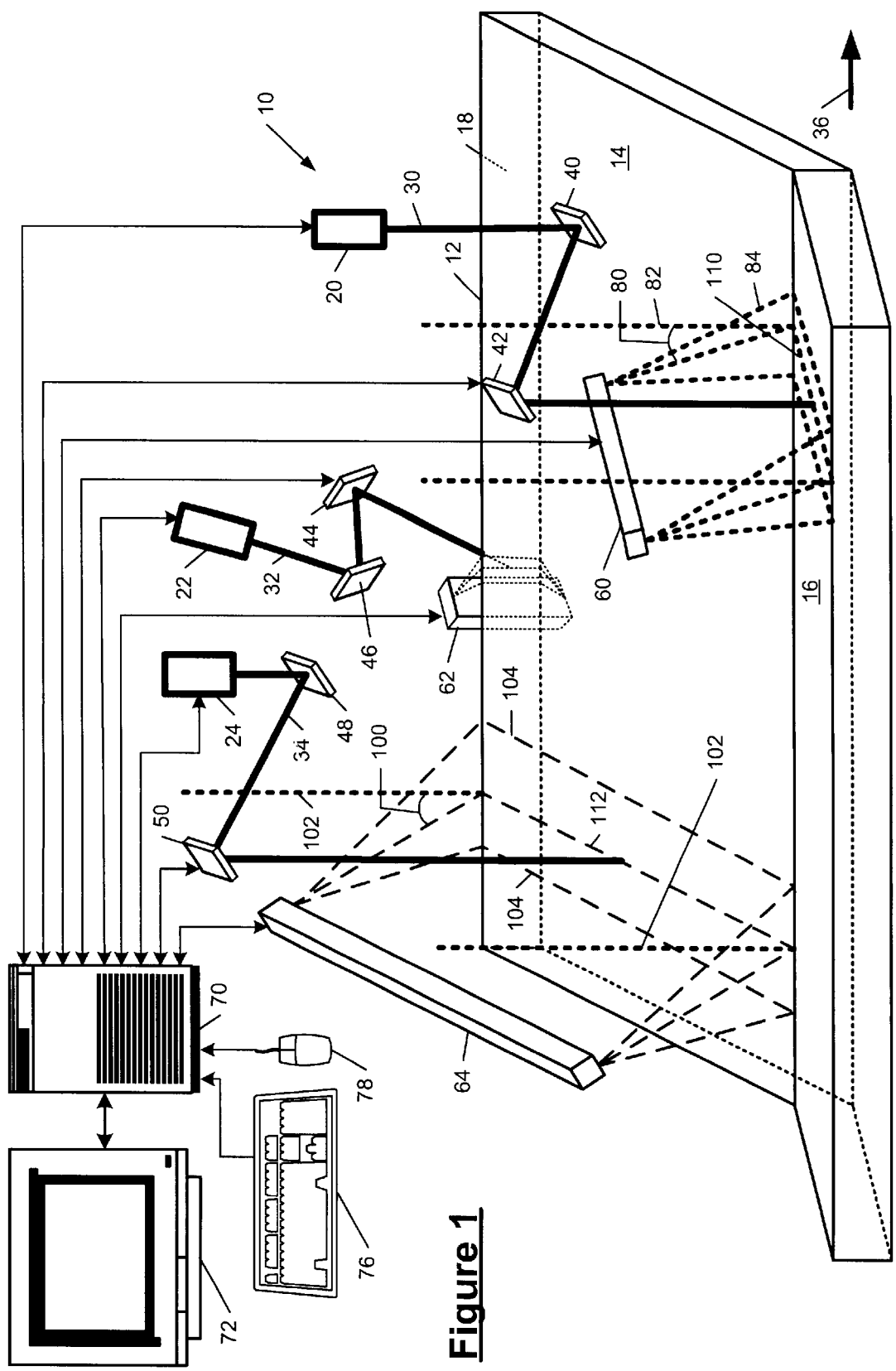
FIG. 1 illustrates an infrared crack detection system according to the present invention.

Referring now to FIG. 1, an infrared crack detection system 10 that identifies surface irregularities such as surface cracks, pits, scratches and holes in a part 12 is shown.

The part 12 includes a plurality of surfaces 14, 16 and 18 which are to be inspected. The part 12 is made of a highly reflective material with a relatively low emissivity. Materials such as aluminum, titanium, and silicon (for example silicon solar panels) have a relatively high reflectivity and low emissivity. The infrared crack detection system 10 includes one or more lasers 20, 22, and 24 which generate a laser beam 30, 32, and 34. A beam diameter of the laser beams 30, 32 and 34 is preferably 50 microns or less. Preferably the lasers 20, 22 and 24 operate between 1 and 10 W. A part transport system (FIG. 2) moves the part 12 in a direction indicated by arrow 36.

The infrared crack detection system further includes mirrors 40, 42, 44, 46, 48 and 50. The mirrors 40, 42, 44, 46, 48 and 50 include fixed and/or movable mirrors as will be described further below. One or more infrared linear detectors 60, 62, and 64 sense light that lies in an infrared region of the light spectrum. Alternately, infrared cameras can be used. A computer 70 includes a display 72, a microprocessor (FIG. 2), memory (FIG. 2) one or more input devices such as a keyboard 76 and a mouse 78.

Preferably, the infrared linear detector 60 is positioned at an angle (identified at 80) relative to a line (identified at 82) that is perpendicular to the surface 16. The infrared linear detector 60 has a linear field of view 84. The infrared linear detector 62 is positioned at an angle relative to a line that is perpendicular to the surface 18 in a similar manner. The infrared linear detector 62 has a linear field of view of the surface 18. The infrared linear detector 64 is positioned at an angle (identified at 100) relative to a line (identified at 102) that is perpendicular to the surface 14. The infrared linear detector 64 has a linear field of view 104.

In use, the laser 20 generates the laser beam 30 that is reflected by the mirrors 40 and 42 onto the surface 16. The mirrors 40 and 42 scan the laser beam 30 across the surface 16 of the part 12. Preferably, the laser beam 30 strikes the surface 16 at an angle that is approximately perpendicular to the surface 16. One or both of the mirrors 40 and 42 can be a multifaceted surface that is rotated to scan the laser beam 30 linearly across the surface 16 in a conventional manner (for example across a line 110 that is within the field of view 84 of the infrared camera 60).

The laser 22 generates the laser beam 32 that is directed by the mirrors 44 and 46 onto the surface 18. The mirrors 44 and 46 scan the laser beam 32 across the surface 18 of the part 12. Preferably the laser beam 32 strikes the surface 18 at an angle that is approximately perpendicular to the surface 18. One or both of the mirrors 44 and 46 can be a multifaceted surface that is rotated to scan the laser beam in a conventional manner.

The mirrors 48 and 50 direct the laser beam 34 onto the surface 14. The mirrors 48 and 50 scan the laser beam 34 across the surface 14 of the part 12. Preferably the mirrors 48 and 50 scan the laser beam 32 across a line 112. Preferably the laser beam 34 strikes the surface 14 at an angle that is perpendicular to the surface 14. One or both of the mirrors 48 and 50 can be a multi-faceted surface that is rotated to scan the laser beam 34 in a conventional manner.

Because the part 12 is made of a highly reflective material, approximately 90 to 95 percent of the energy of the laser beam is reflected. When a surface irregularity such as a crack, pit, scratch and/or hole is encountered, a lower percentage of the laser beam is reflected. The difference in energy is absorbed by the surface irregularity. The surface irregularity becomes a cavity radiator. As can be appreciated, the infrared crack detection system 10 does not depend on the identification of abrupt discontinuities in a thermal gradient of the material. The coupling of the laser in areas surrounding the surface irregularity are irrelevant in the present invention and critical in conventional infrared crack detection.

Localized radiation from the surface irregularity will be detected by the infrared camera. The localized radiation is caused by the surface imperfection absorbing more of the laser beam energy than the surrounding area. As a result, the surface irregularity will also radiate more energy than the surrounding area. The surface imperfection behaves like a cavity radiator or a small gray body. The following formula represents the energy emitted by a gray body:

$$\in = \epsilon \sigma T^4 (F) \cos\theta$$

$\in$ is the energy emitted by gray body, $\sigma$ is the Stefan-Boltzmann constant. $\epsilon$ is the material emissivity. $\theta$ is the angle of the incident laser relative to a line perpendicular to the surface. Where d is the crack depth, $r_1$ is a distance from a crack axis point inside a cone under consideration and $r_2$ is crack opening width. Energy radiated by a gray body is described further in "Engineering Radiation and Heat Transfer" by J. A. Wiebelt, Holt, Rienhart, and Winston, 1966 which is hereby incorporated by reference. Assuming the crack is a cone, F is a configuration factor defined by:

$$F = \tfrac{1}{2}(1-(x-2E^2D^2).(x^2-4E^2D^2)^{-1/2}$$

$$E = r_2/d \text{ and } D = d/r_1$$

$$X = 1 + (1+E^2)D^2$$

Figure 2:
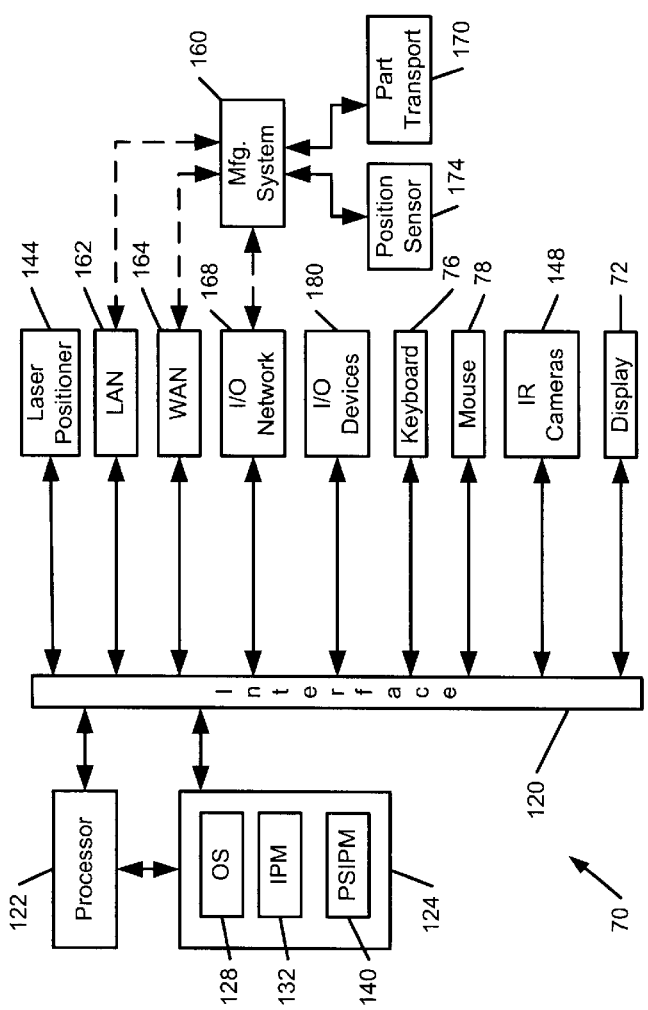
FIG. 2 illustrates a functional block diagram of an infrared crack detection system according to the invention.

Referring now to FIG. 2, the infrared crack detection system 10 is illustrated in further detail. The computer 70 includes an input/output interface 120 that is connected to a processor 122 and memory 124. The memory 124 contains an operating system module 128, an image processing module 132 and a peak storage image processing module 140.

The lasers 20, 22 and 24 (collectively identified at 144 in FIG. 2) are connected to the input/output interface 120. The infrared linear detectors 60, 62 and 64 (collectively identified at 148) are also connected to the input/output interface 120. The display 72, the keyboard 76 and the mouse 78 are also connected to the input/output interface 120. The computer 70 can also be connected to a manufacturing system 160 through a local area network 162, a wide area network 164, and/or an input/output network 168 such as an Ethernet network. The manufacturing system 160 is connected to a part transport system 170 such as a conveyor. The manufacturing system 160 can also be connected to one or more position sensors 174 that generate signals that identify a location of parts 12 travelling on the part transport device 170. The computer 70 is connected to one or more other input/output devices 180 such as printers, scanners, etc. The position sensors 174 may be attached as one of the I/O devices 180 if desired. The image processing module 132 performs conventional image processing on outputs of the infrared cameras 60, 62 and 64. Alternately, the output of the infrared linear detectors 60, 62 and 64 can be output directly to the display 72.

Figure 3:
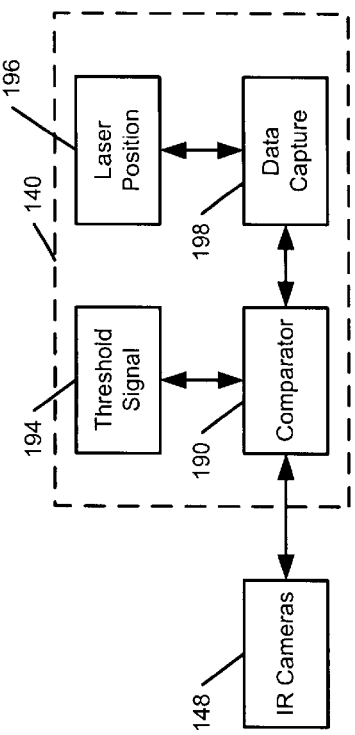
FIG. 3 illustrates a functional block diagram of a peak storage image processor according to the present invention.

The peak storage image processing module 140 is illustrated further in FIG. 3. Outputs of the infrared linear detectors 60, 62 and 64 (collectively identified at 148) are input to a comparator 190. A threshold signal generator 194 generates a threshold signal which identifies surface irregularities that are sufficiently large. The threshold signal is set high enough to eliminate noise and surface irregularities that are within specifications for the part. A laser position generator 196 generates a position signal related to the current scanning position of the laser beam on the part. The position signals and comparator output identify which portions of the part have the surface irregularities for output directly to the display or for storage. When the signal generated by the infrared camera 148 exceeds the threshold signal, the comparator generates a signal that is output to the data capture module 198.

The threshold signal generator 194, the laser position generator 196, the comparator 190, and the data capture module 198 can be implemented as a stand alone module, a device or software executed by the 122 processor.

Figure 4:
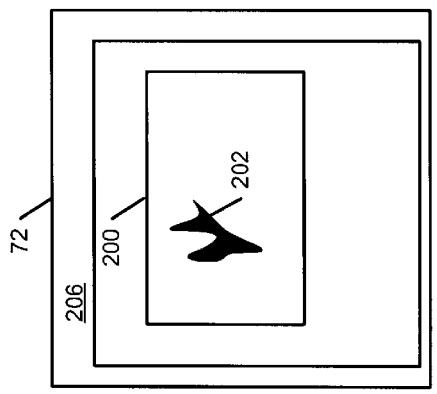
FIG. 4 illustrates a peak storage image output by a display.

Referring now to FIG. 4, the computer 70 collects data related to a part from the data capture module 198 for output on the display 72. The computer 70 generates a graphical representation of a part at 200 and a graphical representation of a surface irregularity at 202. The location of the surface irregularity 202 relative to the part 200 is provided. X and Y coordinates can be provided along with zoom in, zoom out, and other functions generally provided by toolbars and menu bars 206 with conventional drawing or design programs.

In use, the computer or a switch (not shown) actuates the lasers 20, 22 and 24 which generate the laser beams. The mirrors scan the lasers across the surfaces of the part as the part transport moves the part. The infrared cameras generate infrared images of the scanned surfaces of the part. As the laser beam is incident upon surface irregularities, energy is radiated by the surface irregularities. The radiation by the surface irregularity raises the temperature of the surface irregularity above the ambient temperature of the surroundings. The infrared camera captures an infrared image that is output to a display and/or image processing is performed. Surface irregularities are readily identifiable. When coupled with position sensors, the system identifies and stores the location of the surface irregularities relative to the part.

As can be appreciated, the present invention solves the problem of identifying surface irregularities in parts made of highly reflective materials with low emissivity. Surface irregularities can be identified in a production line in real time without contamination or other time consuming processes. Surface irregularities in the order of 10 microns can be detected. In the production of stringers, the system can identify surface irregularities while the part is being transported by the part transport system at 30 inches per minute.

Those skilled in the art can now appreciate from the foregoing description that the broad teachings of the present invention can be implemented in a variety of forms. Therefore while this invention has been described in connection with particular examples thereof, the true scope of the invention should not be so limited since other modifications will become apparent to the skilled practitioner upon a study of the drawings, the specification and the following claims.

What is claimed is:

1. A detection system for identifying surface irregularities in a part, comprising:
    a part having an outer surface that is made of a material having a relatively high reflectivity and a relatively low emissivity;
    a laser source that generates a laser beam having a beam diameter that is approximately 50 microns or less and laser power between 1 and 10 W;
    a scanning device for scanning said laser beam across said outer surface of said part in a first plane that is substantially perpendicular to said outer surface of said part, wherein a surface irregularity in said outer surface acts as a gray body radiator and radiates energy that is absorbed from said laser beam;
    an infrared receiver that is oriented at a fixed first angle relative to said first plane, that is directed at said outer surface of said part, and that generates an infrared signal of said outer surface, wherein said fixed first angle is greater than 0 degrees; and
    a part transport device for moving said part in a first direction that is perpendicular to said first plane.

2. The detection system of claim 1 wherein said infrared receiver is an infrared linear array.

3. The detection system of claim 1 wherein said infrared receiver is oriented at a fixed first angle relative to said first plane.

4. The detection system of claim 3 wherein said first angle is approximately greater than 20 degrees and less than 30 degrees.

5. The detection system of claim 1 further comprising:
    a computer connected to said infrared receiver and said scanning device that includes a processor and memory.

6. The detection system of claim 5 further comprising:
    an image processing module associated with said computer that performs image processing on said infrared signal.

7. The detection system of claim 5 further comprising:
    peak detection image processor associated with said computer that identifies a surface irregularity by comparing said infrared signal generated by said infrared receiver to a threshold signal and by declaring a surface irregularity when said infrared signal exceeds said threshold signal.

8. The detection system of claim 1 wherein said material contains at least one of titanium, aluminum, and silicon.

9. The detection system of claim 1 wherein said part has a thickness that is greater than approximately ⅛ inch.

10. The detection system of claim 1 wherein said scanning device includes a first mirror and a second mirror, wherein one of said first and second mirrors is rotatable and includes a plurality of facets.

11. A system for detecting surface irregularities in a part, comprising:
    a part having an outer surface that is made of a material having a relatively high reflectivity and a relatively low emissivity and a thickness that is greater than ⅛ inch;
    a laser source that generates a laser beam with a beam diameter that is approximately 50 microns or less and a laser power between 1 and 10 W;
    a scanning device for scanning said laser beam across said outer surface of said part in a first plane that is substantially perpendicular to said outer surface of said part, wherein a surface irregularity in said outer surface acts as a gray body radiator and radiates energy from said laser beam;
    an infrared camera that is oriented at a fixed first angle relative to said first plane, that is directed on said surface of said part, and that generates an infrared signal of said outer surface, wherein said fixed first angle is greater than 20 degrees and less than 30 degrees; and
    a part transport that moves said part in a second direction that is perpendicular to said first plane.

12. The method of claim 11 wherein said first angle is greater than 20 degrees and less than 30 degrees.

13. A method for detecting surface irregularities in a part comprising the steps of:

providing a part having an outer surface that is made of a material having a relatively high reflectivity and a relatively low emissivity;

generating a laser beam having a beam diameter that is approximately 50 microns or less and a laser power between 1 and 10 W;

scanning said laser beam across said outer surface of said part in a first plane that is substantially perpendicular to said outer surface of said part, wherein a surface irregularity in said outer surface acts as a gray body radiator and radiates energy from said laser beam;

generating an infrared signal of said outer surface using an infrared receiver that is oriented at a fixed first angle relative to said first plane, wherein said fixed first angle is greater than 0 degrees;

identifying surface irregularities from said infrared image signal; and moving said part in a second direction that is perpendicular to said first plane.

14. The method of claim 13 wherein said material has a thickness that is greater than 1/8 inch and contains at least one of titanium, aluminum, and silicon.

15. The method of claim 13 further comprising the step of:

generating a threshold signal;

comparing said infrared signal to said threshold signal; and declaring a surface irregularity when said image signal exceeds said threshold signal.

16. A detection system for identifying surface irregularities in a part, comprising:

a part having an outer surface that is made of a material having a relatively high reflectivity and a relatively low emissivity, wherein said outer surface includes surface irregularities;

a laser source that generates a laser beam with sufficient power to create a gray body radiator;

a scanning device for scanning said laser beam across said outer surface of said part in a first plane that is substantially perpendicular to said outer surface of said part, wherein said surface irregularities in said outer surface act as a gray body radiator and radiate energy that is absorbed from said laser beam;

an infrared receiver that is oriented at a fixed first angle relative to said first plane, that is directed at said outer surface of said part, and that generates an infrared signal of said outer surface, wherein said fixed first angle is greater than 0 degrees; and a part transport device for moving said part in a first direction that is perpendicular to said first plane.

* * * * *